United States Patent
Kimzey (10) Patent No.: US 11,035,862 B2
(45) Date of Patent: Jun. 15, 2021

(54) USE OF MILD ELECTROPHILES TO REDUCE ARTIFACTS IN ANALYZING GLYCANS RELEASED FROM GLYCOPROTEINS OR GLYCOPEPTIDES

(71) Applicant: ProZyme, Inc., Hayward, CA (US)

(72) Inventor: Michael J. Kimzey, Laguna Hills, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 168 days.

(21) Appl. No.: 16/322,900

(22) PCT Filed: Aug. 16, 2017

(86) PCT No.: PCT/US2017/047229
§ 371 (c)(1),
(2) Date: Feb. 1, 2019

(87) PCT Pub. No.: WO2018/035271
PCT Pub. Date: Feb. 22, 2018

(65) Prior Publication Data
US 2019/0170763 A1 Jun. 6, 2019

Related U.S. Application Data (60) Provisional application No. 62/376,344, filed on Aug. 17, 2016.

(51) Int. Cl.
| | | |
|---|---|---|
| G01N 33/58 | (2006.01) | |
| G01N 33/68 | (2006.01) | |
| G01N 33/53 | (2006.01) | |
| C09B 19/00 | (2006.01) | |
| C09B 57/02 | (2006.01) | |
| C09B 57/08 | (2006.01) | |
| C12P 19/04 | (2006.01) | |

(52) U.S. Cl.
CPC ......... *G01N 33/6848* (2013.01); *C09B 19/00* (2013.01); *C09B 57/02* (2013.01); *C09B 57/08* (2013.01); *C12P 19/04* (2013.01); *G01N 33/5308* (2013.01); *G01N 33/582* (2013.01); *G01N 33/6854* (2013.01); *G01N 2400/10* (2013.01)

(58) Field of Classification Search
CPC ......... C09B 57/08; C09B 19/00; C09B 57/02; C12P 19/04; G01N 33/6848; G01N 33/6854; G01N 33/5308; G01N 33/582; G01N 2400/10

See application file for complete search history.

(56) References Cited

U.S. PATENT DOCUMENTS

| | | |
|---|---|---|
| 3,694,234 A | 9/1972 | Jones |
| 2005/0186645 A1 | 8/2005 | Amor |
| 2006/0217804 A1 | 9/2006 | Dove |
| 2010/0196940 A1 | 8/2010 | Collins |
| 2012/0107942 A1 | 5/2012 | Baginski |
| 2012/0271068 A1 | 10/2012 | Magerlein |
| 2013/0171658 A1 | 7/2013 | Fulton |
| 2014/0179011 A1 | 6/2014 | Brousmiche et al. |
| 2015/0110771 A1 | 4/2015 | Garrido et al. |

OTHER PUBLICATIONS

User Guide. AdvanceBio N-glycan sample preparation kit user guide (24 samples). Agilent Technologies, Inc. 2015, USA, pp. 1-15. (Year: 2015).*
Gong et al. N-glycosylamine-mediated isotope labeling for mass spectrometry-based quantitative analysis of N-linked glycans. Anal Bioanal Chem 2013, vol. 405, pp. 5825-5831. (Year: 2013).*
EPO Extended European Search Report for EP Application 17842084.0, dated Mar. 23, 2020.
Anumula, K.R., Quantitative glycan profiling of normal human plasma derived immunoglobulin and its fragments Fab and Fc, J Immunol Methods, 2012, 167-176, v. 382.
Gimenez, E., Quantitative analysis of N-glycans from human alfa-acid-glycoprotein using stable isotope labeling and zwitter . . . , Analytica Chimica Acta, 2015, 59-68, v. 866.
Duke et al., "N-Glycan Composition Profiling for Quality Testing of Biotherapeutics," Biopharm International, Dec. 2015, 6 pages, Advanstar Communications, Inc.
Young, Lee W., International Search Report, PCT/US2017/047229, dated Jan. 4, 2018, ISA/US.
Young, Lee W., Written Opinion, PCT/US2017/047229, dated Jan. 4, 2018, ISA/US.

* cited by examiner

*Primary Examiner* — Shafiqul Haq
(74) *Attorney, Agent, or Firm* — Laurence J. Hyman; Hyman IP Law (57) ABSTRACT

The presence of mild electrophiles, such as aldehydes, during the denaturation of glycoproteins or glycopeptides and subsequent enzymatic deglycosylation reduces artifacts in subsequent analyses of the glycans released from the glycoproteins or glycopeptides.

38 Claims, 4 Drawing Sheets

USE OF MILD ELECTROPHILES TO REDUCE ARTIFACTS IN ANALYZING GLYCANS RELEASED FROM GLYCOPROTEINS OR GLYCOPEPTIDES

CROSS-REFERENCE TO RELATED APPLICATIONS

This application claims the benefit of U.S. Provisional Patent Application No. 62/376,344, filed Aug. 17, 2016, the contents of which are incorporated herein by reference for all purposes.

STATEMENT OF FEDERAL FUNDING

Not applicable.

BACKGROUND OF THE INVENTION

This invention relates to the field of improving labeling of nucleophilic biomolecules by electrophilic labels, and particularly to labeling glycosylamines.

Many of the proteins produced by eukaryotic cells are modified after translation by the addition of covalently-linked, linear or branched chains of carbohydrates. These protein-carbohydrate conjugates are referred to as glycoproteins; the point at which the carbohydrate is attached is referred to as a glycosylation site. Attached polysaccharides or oligosaccharides are referred to as glycans. A wide range of glycans are found on the different glycosylation sites of particular glycoproteins. The particular pattern of glycans on a particular glycoprotein is determined by the specific cell line that produced the protein and the conditions under which the cells were grown.

Since the glycans conjugated to a protein can affect characteristics critical to its function, including pharmacokinetics, stability, bioactivity, or immunogenicity, it is important in many uses to determine which glycans are present. Thus, the ability to remove some or all of the glycans from a protein and to analyze the glycans to determine their composition is useful for determining whether the glycoprotein will have its desired effect. For example, the Food and Drug Administration ("FDA") requires characterization of carbohydrates attached to biologics (such as therapeutic glycoproteins and vaccines) to show composition of matter and consistency of manufacture, resulting in a need for extensive characterization of the product. Analysis of the profile of the released carbohydrates is also important for quality control in the production of recombinant proteins, in which a change in carbohydrate profile may indicate stress in the system, signaling conditions that may require a commercial-scale fermenter of expensive protein to be discarded. There is therefore considerable interest by biochemists, clinical chemists and pharmaceutical manufacturers in determining the distribution profiles of glycans in biological samples, such as therapeutic glycoproteins.

Glycans are typically attached to glycoproteins in one of two ways. In the first, referred to as N-glycans, the glycans are attached through an N-glycosidic bond at an asparagine residue. In the second, referred to as O-glycans, glycans are attached to an oxygen atom on an amino acid residue. For example, N-acetyl-galactosamine can be enzymatically attached to an oxygen on a serine or a threonine residue.

N-glycans can be enzymatically released from glycoproteins by enzymatic cleavage by various enzymes, such as PNGase F (Peptide-N4-(acetyl-β-glucosaminyl)-asparagine amidase, EC 3.5.1.52.). Enzymatic digestion of N-glycans, such as by PNGase F, typically occurs in an aqueous solution, and results in the initial release of the N-glycans as β-glycosylamines, in which the free-reducing end of the released glycan is conjugated with ammonia (see, e.g., Tarentino, et al. TIGG 1993, 23, 163-170; Rasmussen J. R. J. Am. Chem. Soc. 1992, 114, 1124-1126; Risley, et al. J. Biol. Chem. 1985, 260, 15488-15494, 1985). PNGase F-released N-glycans can be labeled by reductive amination, in which the free-reducing end of a glycan is conjugated to the free amino group of a label, such as a fluorescent dye or a electrical charge, or by use of an amine-reactive dye. Depending on the label used, the labeled glycans can then be analyzed by any of a variety of analytical methods, such as high performance liquid chromatography ("HPLC"), capillary electrophoresis ("CE"), carbohydrate gel electrophoresis, or mass spectrometry ("MS"). Labeling of N-glycans is taught, for example, in co-owned U.S. Pat. Nos. 8,124,792 and 8,445,292.

Many protocols use a so-called "one pot" procedure, in which glycans are released as glycosylamines, which are then labeled for analysis in the presence of the now aglycosylated or partially glycosylated glycoprotein. Unfortunately, proteins contain reactive nucleophilic N-termini and amino acids, such as lysines, which have nucleophilic side chains. Since the aglycosylated or partially glycosylated glycoprotein is still present in the solution, the N-termini and reactive side chains of the amino acids on the protein may also be labeled, resulting in a protein with multiple labels. These labeled proteins may exhibit similar physicochemical properties to the labeled glycosylamines. The labeled proteins may be difficult to separate from the labeled glycans, and may coelute and comigrate on HPLC or capillary electrophoresis, respectively. This can result in artifacts that make it difficult to quantify the glycans of interest There remains a need for compositions and methods that improve labeling of glycosylamines and other nucleophiles. Surprisingly, the present invention meets these and other needs.

BRIEF SUMMARY OF THE INVENTION

In a first group of embodiments, the invention provides in vitro methods of labeling glycosylamines released from a glycoprotein or glycopeptide of interest, the method comprising: (a) forming a mixture of the glycoprotein or glycopeptide and a mild electrophile in a solution, (b) incubating the mixture in the solution at a first temperature and for a time sufficient to denature the glycoprotein or glycopeptide, (c) reducing the temperature of the mixture in the solution to a second temperature, which second temperature is suitable for enzymatic deglycosylation of the glycoprotein or glycopeptide, (d) contacting the glycoprotein or glycopeptide at the second temperature with at least one deglycosylation enzyme which releases glycans from a glycoprotein or glycopeptide as glycosylamines, thereby releasing glycans from the glycoprotein or glycopeptide as glycosylamines, and (e) contacting the released glycosylamines with an amine-reactive dye under conditions allowing the amine-reactive dye to label the released glycosylamines, thereby labeling the released glycosylamines. In some embodiments, the first temperature is 90° C. or higher. In some embodiments, the solution further comprises a detergent. In some embodiments, the at least one deglycosylation enzyme which releases glycans from said glycoprotein or glycopeptide as glycosylamines is PNGase F. In some embodiments, the mild electrophile is DL-glyceraldehyde, glyceraldehyde dimer, glycoaldehyde dimer, erythrose, pyruvaldehyde, 2-ethylbutyraldehyde, 2-methylbutyraldehyde, 2-methylvaleraldehyde, 4-methyl-4-nitrovaleraldehyde, acetaldehyde, butyraldehyde, isobutyraldehyde, propionaldehyde, or valeraldehyde. In some embodiments, the mild electrophile is DL-glyceraldehyde, glyceraldehyde dimer, or glycoaldehyde dimer. In some embodiments, the mild electrophile is DL-glyceraldehyde. In some embodiments, the mild electrophile is glyceraldehyde dimer. In some embodiments, the mild electrophile is glycoaldehyde dimer. In some embodiments, the glycoprotein of interest is an antibody. In some embodiments, the contacting of released glycosylamines with the amine-reactive dye in step (e) is within 30 minutes of release from the glycoprotein or glycopeptide. In some embodiments, the contacting of released glycosylamines with the amine-reactive dye in step (e) is within 15 minutes of release from the glycoprotein or glycopeptide. In some embodiments, the contacting of released glycosylamines with the amine-reactive dye in step (e) is within 1 minute of release of the glycosylamines from the glycoprotein or glycopeptide. In some embodiments, the amine-reactive dye is selected from the group consisting of (2-(diethylamino) ethyl 4-[(2,5-dioxopyrrolidin-1-yl)oxycarbonylamino]benzoate) (InstantPC™) 8-[(2,5-dioxopyrrolidin-1-yl)oxycarbonylamino]naphthalene-1,3,5-trisulfonic acid ("Amine-reactive ANTS™"), 4-[(2,5-dioxopyrrolidin-1-yl) oxycarbonylamino]benzoic acid ("InstantAA™"), (7-[(2,5-dioxopyrrolidin-1-yl)oxycarbonylamino]naphthalene-1,3,6-trisulfonic acid) ("InstantQ™"), and RAPIFLUOR-MS®. In some embodiments, the released glycosylamines are at or at about room temperature when contacted with the amine-reactive dye. In some embodiments, the method further comprises either: step (f), providing the labeled glycosylamines to an analytical means, or, step (f') subjecting the labeled glycosylamines to a solid phase extraction means that reduces the amount of mild electrophile present, to obtain labeled glycosylamines with a reduced amount of the mild electrophile present, and step (f") providing the labeled glycosylamines with the reduced amount of the mild electrophile present to an analytical means. In some embodiments, the solid phase extraction means is a solid phase cartridge. In some embodiments, the analytical means is selected from the group consisting of high-pressure liquid chromatography, capillary electrophoresis, fluorescence analysis, mass spectrometry, and a combination of any of these. In some embodiments, the glycoprotein of interest is in a biological sample. In some embodiments, the biological sample is selected from the group consisting of: a cell culture supernatant, a membrane protein preparation, milk, a tissue sample, cerebrospinal fluid, plasma, serum, urine, a respiratory secretion, bile synovial fluid, pleural fluid, lymph, tears, saliva, and a stool sample. In some embodiments, the biological sample is milk.

In a further group of embodiments, the invention provides compositions comprising: (i) a detergent, (ii) a mild electrophile, (iii) at least one deglycosylation enzyme which releases glycans from the glycoprotein as glycosylamines, (iv) a partially or fully deglycosylated protein or peptide from which glycans have been removed by the deglycosylation enzyme, and (v) glycosylamines released from the partially or fully deglycosylated protein by the enzyme. In some embodiments, the glycoprotein is an antibody. In some embodiments, the deglycosylation enzyme is PNG F. In some embodiments, the mild electrophile is DL-glyceraldehyde, glyceraldehyde dimer, glycoaldehyde dimer, erythrose, pyruvaldehyde, 2-ethylbutyraldehyde, 2-methylbutyraldehyde, 2-methylvaleraldehyde, 4-methyl-4-nitrovaleraldehyde, acetaldehyde, butyraldehyde, isobutyraldehyde, propionaldehyde, or valeraldehyde. In some embodiments, the mild electrophile is DL-glyceraldehyde, glyceraldehyde dimer, or glycoaldehyde dimer. In some embodiments, the mild electrophile is DL-glyceraldehyde.

In another group of embodiments, the invention provides in vitro methods of reducing artifacts in analyzing glycans released from a glycoprotein or glycopeptide and labeled by reductive amination, said method comprising the following steps in the following order: (a) forming a solution comprising the glycoprotein or glycopeptide, and a mild electrophile, under conditions allowing said mild electrophile to block any nucleophilic components present in the solution or on the glycoprotein or glycopeptide, (b) heating the solution to a first temperature, and for a time, sufficient to denature the glycoprotein or glycopeptide, (c) reducing the temperature of the solution to a second, cooler temperature, (d) releasing glycans from said glycoprotein or glycopeptide, (e) labeling the glycans released from the glycoprotein or glycopeptide by reductive amination, and (f) analyzing the glycans labeled by the reductive amination, whereby blocking of the nucleophilic components present in the solution or on the glycoprotein or glycopeptide prior to the denaturation and reductive amination reduces artifacts in the analysis of the released glycans. In some embodiments, the mild electrophile is DL-glyceraldehyde, glyceraldehyde dimer, glycoaldehyde dimer, erythrose, pyruvaldehyde, 2-ethylbutyraldehyde, 2-methylbutyraldehyde, 2-methylvaleraldehyde, 4-methyl-4-nitrovaleraldehyde, acetaldehyde, butyraldehyde, isobutyraldehyde, propionaldehyde, or valeraldehyde. In some embodiments, the mild electrophile is DL-glyceraldehyde, glyceraldehyde dimer, or glycoaldehyde dimer. In some embodiments, the mild electrophile is DL-glyceraldehyde. In some embodiments, the mild electrophile is glyceraldehyde dimer. In some embodiments, the mild electrophile is glycoaldehyde dimer. In some embodiments, the glycoprotein is an antibody. In some embodiments, the glycoprotein of interest is in a biological sample. In some embodiments, the biological sample is selected from the group consisting of: a cell culture supernatant, a membrane protein preparation, milk, a tissue sample, cerebrospinal fluid, plasma, serum, urine, a respiratory secretion, bile synovial fluid, pleural fluid, lymph, tears, saliva, and a stool sample. In some embodiments, the biological sample is milk. In some embodiments, the solution further comprises a detergent. In some embodiments, the analysis is selected from the group consisting of high-pressure liquid chromatography, capillary electrophoresis, fluorescence analysis, mass spectrometry, and a combination of any of these.

In yet a further group of embodiments, the invention provides methods of reducing artifacts in analyzing glycans released from a glycoprotein or glycopeptide without labeling, comprising the following steps in the following order: (a) forming a solution comprising the glycoprotein or glycopeptide, and a mild electrophile, under conditions allowing the mild electrophile to block any nucleophilic components present in the solution or on the glycoprotein or glycopeptide, (b) heating the solution to a first temperature, and for a time, sufficient to denature said glycoprotein or glycopeptide, (c) reducing the temperature of said solution to a second, cooler temperature, (d) releasing glycans from the glycoprotein or glycopeptide, and (e) analyzing the released glycans, whereby said blocking of said nucleophilic components present in said solution or on said glycoprotein or glycopeptide prior to said denaturation reduces artifacts in said analysis of said released glycans. In some embodiments, the analysis is by mass spectrometry, High-performance Anion Exchange Chromatography coupled with Pulsed Amperometric Detection ("HPAE-PAD"), Charged Aerosol Detection ("CAD"), Evaporative Light Scattering Detection ("ELSD"), or a combination of any of these.

In still another group of embodiments, the invention provides kits for labeling glycosylamines released from a glycoprotein or glycopeptide, comprising, (a) a mild electrophile, (b) an amine-reactive dye, an agent for performing reductive amination, or both an amine-reactive dye and an agent for performing reductive amination, and (c) instructions on denaturing said glycoprotein or glycopeptide in the presence of the mild electrophile. In some embodiments, the agent for performing reductive amination is anthranilic acid ("2-AA"). In some embodiments, the agent for performing reductive amination is 2-aminobenzamide ("2-AB"). In some embodiments, the kit further comprises a deglycosylation enzyme. In some embodiments, the deglycosylation enzyme is PNGase F. In some embodiments, the mild electrophile is DL-glyceraldehyde, glyceraldehyde dimer, glycoaldehyde dimer, erythrose, pyruvaldehyde, 2-ethylbutyraldehyde, 2-methylbutyraldehyde, 2-methylvaleraldehyde, 4-methyl-4-nitrovaleraldehyde, acetaldehyde, butyraldehyde, isobutyraldehyde, propionaldehyde, or valeraldehyde. In some embodiments, the mild electrophile is DL-glyceraldehyde, glyceraldehyde dimer, or glycoaldehyde dimer. In some embodiments, the said mild electrophile is DL-glyceraldehyde. In some embodiments, the amine-reactive dye is selected from the group consisting of (2-(diethylamino)ethyl 4-[(2,5-dioxopyrrolidin-1-yl)oxycarbonylamino]benzoate) (InstantPC™), 8-[(2,5-dioxopyrrolidin-1-yl)oxycarbonylamino]naphthalene-1,3,5-trisulfonic acid ("InstantANTS™"), 4-[(2,5-dioxopyrrolidin-1-yl)oxycarbonylamino]benzoic acid ("InstantAA™"), (7-[(2,5-dioxopyrrolidin-1-yl)oxycarbonylamino]naphthalene-1,3,6-trisulfonic acid) ("7-ANTS"), and RAPIFLUOR-MS®.

DETAILED DESCRIPTION

Analysis of the glycans attached to glycoproteins or glycopeptides has become important for meeting FDA requirements regarding showing composition of matter and consistency of manufacture of therapeutic glycoproteins and for providing quality control during the production of recombinant glycoproteins. As described in the Background, for speed convenience and cost-savings, N-glycans present on a glycoprotein or glycopeptide of interest are often analyzed in "one pot" procedures by releasing them from the glycoprotein by enzymatic digestion and then labeling the resulting released glycans, which are released as glycosylamines, with an amine reactive dye in the presence of the now-aglycosylated or partially deglycosylated glycoprotein or glycopeptide. Unfortunately, glycoproteins and glycopeptides contain nucleophilic N-termini and amino acids, such as lysines, with nucleophilic side chains, each of which can also react with amine-reactive dyes and be labeled by the dye. This can be a particular problem with some negatively charged dyes used in capillary electrophoresis, or "CE" analysis. The labeled deglycosylated proteins or peptides may be difficult to separate from the labeled glycans, and may co-elute and co-migrate on HPLC or capillary electrophoresis, respectively and is particularly true for smaller, labelled aglycosylated proteins or peptides, as the dye changes the protein's or peptide's migration characteristics. The labeling of the deglycosylated protein or peptide can result in artifacts that make it difficult to quantify the glycans of interest.

Surprisingly, it has now been found that mild electrophiles, such as small, polar aldehydes, can be used to block the N-termini of glycoproteins or glycopeptides, as well as nucleophilic side chains on amino acids such as lysines, and are particularly useful in blocking the N-termini and nucleophilic side chains or other nucleophilic components of glycoproteins or glycopeptides during heat denaturation. Glycoproteins or glycopeptides with the N-termini and nucleophilic side chains blocked can then be subjected to deglycosylation and labeling of the released glycosylamines with amine-reactive dyes without having the amine-reactive dye also react with the protein's or peptide's blocked N-terminus and nucleophilic side chains. In studies underlying the present disclosure, a surprising and dramatic reduction in artifacts was seen when analyzing the labeled glycans between samples denatured and then deglycosylated and labeled in the presence of an exemplar mild electrophile as compared to a like sample subject to the same protocol, but without the presence of the mild electrophile.

Embodiments of the inventive methods thus reduce the steps needed to analyze glycans released from a glycoprotein or glycopeptide, while at the same time improving the accuracy of the analysis. They reduce the number of steps needed to analyze released glycans by eliminating the need for a step to remove aglycosylated or partially deglycosylated protein or peptide from the solution containing the released glycans prior to labeling with an amine-reactive dye to avoid having lysine residues or other amino acids with a nucleophilic side chain (as well as the free amino end of the protein or peptide) labeled by the dye. They improve the accuracy of analysis of the glycans released from the glycoprotein or glycopeptide in two ways. First, they dramatically reduce artifacts from the labeling of lysine residues or other amino acids with a nucleophilic side chain, or other nucleophilic components of the glycoprotein or glycopeptide, as well as the free amino end of the protein or peptide. Some analytical systems show such labeled proteins and peptides as "humps," rather than sharp peaks, making it harder to quantitate labeled glycans that might co-migrate with the labeled, deglcosylated protein or peptide. Decreasing the labeling of the protein or peptide by blocking the reactive amines with a mild electrophile prior to the labeling reaction reduces or eliminates this problem. Second, when the mixture containing the blocked protein or peptide and the mild electrophile is denatured prior to labeling of the protein or peptide of interest, any remaining mild electrophile is available to react with any trace nucleophiles that may be present in the denaturation mix, rendering the nucleophiles unavailable for reaction with the dye when the labeling step is commenced. This further reduces artifacts during the labeling step.

In some embodiments, the inventive methods comprise the following steps, in the following order. First, the mild electrophile and the glycoprotein or glycopeptide of interest are combined in a solution. Conveniently, this is done by adding the mild electrophile to a solution already containing the glycoprotein or glycopeptide of interest, but the glycoprotein or glycopeptide of interest may instead be added to a solution already containing the mild electrophile, or both may be added to a suitable buffer. The resulting mixture, which may further include detergents and other reagents conventionally used in denaturing proteins or peptides in enzymatic deglycosylation protocols, is then heated to denature the glycoprotein or glycopeptide of interest. Without wishing to be bound by theory, it is believed that heat treatment makes the lysines and possibly the N-terminus of the glycoprotein or glycopeptide more reactive, allowing them to form Schiff bases/hemiaminals with the aldehydes. Without wishing to be bound by theory, it is further believed that the mild electrophile attaches to lysine residues, other nucleophilic components present on the glycoprotein or glycopeptide, the protein's or peptide's N-terminus, or combinations of any of these, blocking the lysine residues, other nucleophilic components, protein N-terminus, or combination of any of these, during subsequent steps of the protocol under the reaction conditions to be employed. (Persons of skill will appreciate that, while each glycoprotein or glycopeptide molecule has only one N-terminus, a plurality of such molecules will be present in any deglycosylation protocol. Thus, a reference to blocking of a glycoprotein's or a glycopeptide's N-termini will be understood by the reader to refer to the N-termini of a plurality of separate glycoprotein or glycopeptide molecules.)

The now-denatured glycoprotein or glycopeptide of interest is then cooled to a temperature suitable for enzymatic deglycosylation and then put in contact with a deglycosylation enzyme selected by the practitioner. For example, the deglycosylation enzyme may be added to the mixture containing the now-denatured protein or peptide of interest, the mixture containing the now-denatured protein or peptide of interest may be added to a reaction vessel containing the enzyme, or the mixture may be flowed over a substrate on which the deglycosylation enzyme has been immobilized. In some embodiments, the contacting of the mixture with the deglycosylation enzyme takes place in a microfluidic apparatus. In some preferred embodiments, the enzyme is the amidase PNGase F, which releases N-glycans as nascent glycosylamines.

The glycosylamines released from the now fully- or partially-aglycosylated protein or peptide of interest are then treated with an amine-reactive dye to label the glycosylamines for analysis. (For convenience of reference, both glycosylamines labeled by amine-reactive dyes and glycans labeled by reductive amination are sometimes referred to herein as "labeled glycans." It will be clear in context if a particular reference refers to only a labeled glycosylamine or a glycan labeled by reductive amination. It is further noted that amine-reactive dyes have been used to label glycosylamines for years and conditions suitable for them to react with and to label glycosylamines are well known in the art.) As the protein or peptide's lysine residues and N-termini have been blocked by the mild electrophile, they are not labeled with the amine-reactive dye. The blocked, aglycosylated protein or peptide therefore does not have to be removed from the solution prior to labeling of the released, labeled glycans, as it will not be labeled and will not introduce artifacts which could otherwise add to the difficulty of identifying or quantifying the labeled glycans.

In some embodiments, the mild electrophile is removed from the solution before labeling the glycosylamines released from the glycoprotein or glycopeptide, such as with an amine-reactive dye. In some embodiments, it is not removed before labeling the glycosylamines. Without wishing to be bound by theory, it is believed that, at the temperatures used in protocols for labeling glycans (typically around 50° C. or lower), the amine-reactive dye outcompetes the mild electrophile in reacting with the glycosylamines.

In some embodiments, the protocol described above may be used for labeling glycans of glycoproteins in a biological sample, rather than glycoproteins that have been purified to be free of the presence of other types of biological molecules. Biological samples containing glycoproteins may come from, for example: cell culture supernatants; membrane protein preparations; milk (which contains glycoproteins and free oligosaccharides); tissue samples, such as biopsies; biological fluids, such as cerebrospinal fluid; plasma; serum; urine; respiratory secretions; bile synovial fluid; pleural fluid; lymph; tears; saliva; or stool samples. Such unpurified samples often contain amine contaminants, such as small amines, nucleophiles, or other unknown reactive compounds. For example, contaminants that are present during reductive amination in significant amounts might create artifacts by competing with an agent such as 2-AB, thereby reducing the labeling of the glycans and the consequent glycan signal during analysis. Similarly, the presence of the contaminants during labeling of glycosylamines with an amine-reactive dye can result labeling of the contaminants, thereby creating labeled artifacts that interfere with the glycan signal of interest. It is expected that adding mild electrophile prior to denaturation blocks these contaminants in the sample, thereby reducing both of these types of artifacts. In preferred embodiments, the denaturation includes heating the sample.

Optionally, the mixture is then subjected to a clean-up step, such as passage through a solid phase cartridge, to remove the mild electrophile. The labeled glycans are typically then provided to an analytical means, such as an apparatus for performing high-pressure liquid chromatography, for capillary electrophoresis, for fluorescence analysis, or for mass spectrometry, to determine the types and amounts of glycans released from the glycoprotein or glycopeptide of interest or from those present in a particular biological sample. Often, a plurality of samples are taken from the mixture so that the glycans released from the glycoprotein or glycopeptide of interest (or from a particular biological sample) can be provided to, and analyzed by, a combination of two or more analytical means.

The scheme below sets forth a schematic showing the blocking of amine nucleophiles using DL-glyceraldehyde as an exemplar mild electrophile.

Use of Mild Electrophiles to Reduce Artifacts in Reductive Amination or in Non-Labeling Procedures

Glycans can also be labeled by reductive amination at their reducing ends. Two labels typically used in the art for labeling by reductive amination are 2-AA (anthranilic acid) and 2-AB (2-aminobenzamide). See, e.g., Bigge J. C., et al., Nonselective and efficient fluorescent labeling of glycans using 2-aminobenzamide and anthranilic acid. Anal. Biochem., 230:229-238 (1995). Since this labeling method does not employ amine-reactive dyes, it does not label the N-terminus of the glycoprotein or amine-containing side chains. However, the amount of glycan available to be labeled by reductive amination can be reduced by interactions of the glycans with reagents which may be present in the labeling solution and which can react with the glycans. For example, Tris, or tris(hydroxymethyl)aminomethane, is commonly used as a constituent of buffer solutions. An excess of Tris in the buffer, however, can allow the Tris to compete with the label, such as 2-AB, in reacting with glycans present in the solution. Similarly, if the solution containing the glycans has not been subjected to sufficient clean-up steps, there could be small molecules, such as peptides, with an amine that may also be able to react with the glycans. Any reduction in the amount of glycans available to be labeled by reductive amination results in an understatement of the amount of glycans present in the sample. It is believed that the presence of a mild electrophile when the glycans are introduced into the solution (such as by chemical release from a glycoprotein) reduces the interaction of the glycans with such reagents, thereby increasing the accuracy of the analysis of the glycans released from the glycoprotein or glycopeptide. Typically, the mild electrophile is added to the solution prior to denaturation of the glycoprotein or glycopeptide.

Since the presence of a mild electrophile can keep reagents or unknown small molecules in the solution from unwanted interactions with glycans, they can also be used to reduce artifacts in situations that do not involve a labeling reaction. For example, interaction of a glycan with a small molecule in the solution could affect the apparent molecular weight of the glycan, throwing off subsequent analysis by mass spectrometry ("MS"). Other analytical techniques known in the art that do not involve labeling the glycans but that can benefit by the presence of a mild electrophile during denaturation of the glycoprotein or glycopeptide include: High-performance Anion Exchange Chromatography coupled with Pulsed Amperometric Detection ("HPAE-PAD"), Charged Aerosol Detection ("CAD"), and Evaporative Light Scattering Detection ("ELSD").

Mild Electrophiles

In some preferred embodiments, the mild electrophile is an aldehyde, such as DL-glyceraldehyde, or glycoaldehyde dimer. In preferred embodiments, the mild electrophile prevents labeling of protein when a protein is in a solution with an amine-reactive dye, and is compatible with the enzyme being used to deglycosylate the glycoprotein or glycopeptide. As used herein, "compatible with the enzyme being used" means that the mild electrophile does not denature the enzyme or reduce its activity to less than 80% of the activity the enzyme has in the absence of the mild electrophile and more preferably does not reduce its activity to less than 90%, 91%, 92%, 93% 94%, 95%, 96%, 97% 98% or 99% of the activity of the enzyme in the absence of the mild electrophile, with each successive higher percentage of activity being more preferred. The percentage of activity of the enzyme of choice can be readily measured to test the compatibility of any particular mild electrophile by dividing a sample into a first and a second aliquot, adding the mild electrophile being tested to the second aliquot but not to the first aliquot, performing denaturation and labeling steps using an amine-reactive dye, and comparing the glycan labeling of the first aliquot compared to that of the second aliquot. Mild electrophiles that cause a reduction in the measurement of the glycans present in the second aliquot to that of the first aliquot are less preferred. An exemplary assay is set forth in the Examples.

In a preferred embodiment, the mild electrophile is DL-glyceraldehyde, shown in Structure 1. As used herein, references to "glyceraldehyde" refer to DL-glyceraldehyde, unless otherwise specified or required by context.

Structure 1

DL-glyceraldehyde

In some embodiments, the mild electrophile is not L-glyceraldehyde. In some embodiments, the mild electrophile is not D-glyceraldehyde.

In a second preferred embodiment, the mild electrophile is glyceraldehyde dimer (3,6-Dihydroxy-1,4-dioxane-2,5-dimethanol), shown below as Structure 2.

Structure 2

In a third preferred embodiment, the mild electrophile is glycoaldehyde dimer, shown in structure 3. In some embodiments, the glycoaldehyde dimer is DL-glycoaldehyde dimer.

Structure 3

As a reagent, glycoaldehyde dimer is sold as a crystalline powder and exists in the form of structure 2. According to Wikipedia, in aqueous solution, glycoaldehyde dimer exists as a mixture of at least four species, which rapidly interconvert.

In some embodiments, other aldehydes can be used as mild electrophiles in the inventive compositions, kits, and methods. These include: erythrose, pyruvaldehyde, 2-ethylbutyraldehyde, 2-methylbutyraldehyde, 2-methylvaleraldehyde, 4-methyl-4-nitrovaleraldehyde, acetaldehyde, butyraldehyde, isobutyraldehyde, propionaldehyde, and valeraldehyde. In preferred embodiments, the aldehyde is not itself fluorescent. Any particular aldehyde or other mild electrophile can be tested, for example in the assays taught in the Examples, to see if it prevents artifact peaks without interfering with the ability to detect labeled glycans.

Deglycosylating Glycoproteins and Glycopeptides

In the inventive methods, N-glycans are preferably released from the glycoprotein or glycopeptide of interest by enzymatic means. Protocols and workflows for releasing N-glycans from glycoproteins using deglycosylation enzymes have been known in the art for years and it is assumed persons of skill are familiar with the ranges of times, temperatures and pH used in those workflows and protocols. An exemplar protocol is set forth in the Examples.

Enzymatic digestion by enzymatic cleavage is typically achieved with an exoglycosidase, an endoglycosidase, or an amidase, such as PNGase F. Exemplar endoglycosidases include endo-alpha-N-acetyl-galactosaminidase, Endoglycosidase F1, Endoglycosidase F2, Endoglycosidase F3, and Endoglycosidase H. In some embodiments, the enzyme is the common deglycosylation enzyme PNGase F (Peptide-N4-(acetyl-β-glucosaminyl)-asparagine amidase, EC 3.5.1.52), which releases N-glycans from the glycoprotein in the form of glycosylamines. The glycosylamines can then be labeled with an amine-reactive dye, as discussed below. Glycosylamines hydrolyze over time. Accordingly, N-glycans released from a glycoprotein as glycosylamines preferably are labeled within 30 minutes of being released from the glycoprotein, with shorter periods, such as about 25 minutes, about 20 minutes, about 15 minutes, or about 10 minutes, being more preferred, in that order, with "about" meaning ±2 minutes. In preferred embodiments, the N-glycans are labeled within about 9, 8, 7, 6, 5, 4, 3, 2 or 1 minutes after being released from the glycoprotein, with "about" meaning ±30 seconds, with each successive shorter period being more preferred. In particularly preferred embodiments, the N-glycans are labeled within 30 seconds after release from the glycoprotein.

Amine-Reactive Labels

As used herein, the terms "amine-reactive labels" and "amine-reactive dyes" are used interchangeably. Both are used to denote reagents that, under appropriate conditions, can covalently attach to an amine, such as the side group of a lysine present on a protein or to a glycosylamine released from a glycoprotein by enzymatic digestion, to provide a tag which can then be detected by an analytical means of choice, such as HPLC or capillary electrophoresis.

A number of amine-reactive dyes are known in the art. The website of Thermo Fisher Scientific (Waltham, Mass.), lists 152 reagents under the label "Amine-Reactive Fluorophores, Biotins, Quantum Dots, & Other Labels," including 1-pyrenebutanoic acid, succinimidyl ester, 2',7'-Difluorofluorescein (Oregon Greene 488), 5(6)-CR 6G, SE (5-(and-6)-Carboxyrhodamine 6G, Succinimidyl Ester), mixed isomers, and 7-Diethylaminocoumarin-3-Carboxylic Acid. ProZyme, Inc. (Hayward, Calif.) sells a variety of amine-reactive labels, including a basic dye, InstantPC™ (2-(diethylamino)ethyl 4-[(2,5-dioxopyrrolidin-1-yl)oxycarbonylamino]benzoate). Two acid labels disclosed in co-owned U.S. Pat. No. 8,124,792 are 8-[(2,5-dioxopyrrolidin-1-yl)oxycarbonylamino]naphthalene-1,3,5-trisulfonic acid (amine-reactive "ANTS™") and 4-[(2,5-dioxopyrrolidin-1-yl)oxycarbonylamino]benzoic acid ("InstantAA™"). Amine-reactive ANTS™ and "InstantQ" (7-[(2,5-dioxopyrrolidin-1-yl)oxycarbonylamino]naphthalene-1,3,6-trisulfonic acid), another dye with three sulfonic acids, add 3 negative charges and a fluorophore to the glycans, which facilitates their separation by capillary electrophoresis and detection. And, Waters Corporation (Milford, Mass.), sells RAPIFLUOR-MS® for labeling glycosylamines. (The compound sold as RAPIFLUOR-MS® is found in U.S. Published Patent Appln. US2014/0179011 A1, on page 14, top left column, in the embodiment where R=N.) It is anticipated that mild electrophiles can be used effectively with each of these amine-reactive labels.

Conditions for Labeling and Analysis of Glycans Released as Glycosylamines

Persons of skill are familiar with methods for rapid labeling of N-glycans released from glycoproteins as glycosylamines under mild conditions. U.S. Pat. No. 8,124,792 (the "'792 patent"), for example, discusses rapid labeling of N-glycans under mild conditions at col. 22, line 24, to col. 23, line 3, and col. 30, Example 10, to col. 32, Example 13, as do the corresponding portions of U.S. Pat. No. 8,445,292 (each of these patents is incorporated herein by reference). Methods for providing labeled glycosylamines to an analytical means are also well-known in the art, as exemplified by the teachings of the '792 patent at col. 23, line 41 to line 67 and col. 32, Examples 13 and 14. Typically, the labeled glycosylamines are analyzed by an analytical means such as high-pressure liquid chromatography, capillary electrophoresis, fluorescence analysis, mass spectrometry, or a combination of two or more of these means. In some embodiments, the combination is of fluorescence analysis and mass spectrometry Removal of the Mild Electrophile In some embodiments, it may be desirable to remove the mild electrophile before subjecting the labeled glycans to analytical techniques such as mass spectrometry. A number of means for removal of reagents, such as mild electrophiles, are known in the art and can be used to remove the mild electrophile prior to analysis of the labeled glycans. In preferred embodiments, the mild electrophile is removed by using a solid phase cartridge or other solid phase extraction ("SPE") device used in the art to remove undesired components from a solution. The labeled glycans are typically loaded onto a selected cleanup cartridge, washed to remove most non-glycan contaminants, and then eluted. Cleanup procedures for labeled glycans are routinely used in the art and it is expected that practitioners are well familiar with them.

Kits

Conveniently, kits can be provided containing a selection of deglycosylation enzymes and one or more mild electrophiles, such as DL-glyceraldehyde or glycoaldehyde dimer, either in dried form or in a solution that can be added directly to a sample of a glycoprotein of interest prior to its denaturation. Conveniently, the kits can further comprise one or more amine-reactive dyes to be used in labeling glycosylamines released by enzymatic digestion of the glycoprotein, or reagents for conducting reductive amination of glycans, such as 2-AB, or both an amine-reactive dye and a reagent, such as 2-AB, for performing reductive amination. The kits can further provide instructions for denaturing the glycoprotein in the presence of the mild electrophile.

EXAMPLES

Example 1

This Example sets forth abbreviations for some of the reagents used in exemplar workflows of deglycosylation and labeling procedures performed using exemplar mild electrophiles in some of the Examples below.

"HEPES": 4-(2-hydroxyethyl)-1-piperazineethanesulfonic acid
"TMD": 1,3-Di(4-pyridyl)propane
"DMF": dimethylformamide
"ACN": Acetonitrile
"NMF": N-methylformamide
"TSH": Bovine Thyrotropic Hormone
"EPO": EPOGEN® (epoetin alfa)

Example 2

This Example sets forth an exemplar workflow for denaturing and deglycosylating a glycoprotein in the presence of an exemplar mild electrophile, and labeling amines released from the glycoprotein by enzymatic digestion. Duplicate sets of assays were run, the first using RNase b as the glycoprotein and the second using TSH as the glycoprotein.

Denaturation Step:

2 µl of 5% fatty acid detergent (tetramethyl ammonium laurate) was added to 20 µl of a solution of 2 mg/ml protein (40 µg of protein).

Samples were divided into two aliquots. To the first aliquot, 2 µl of a solution of 100 mg/ml (DL)-glyceraldehyde in water was added. The second aliquot did not have (DL)-glyceraldehyde added and served as the control.

The reagents were thoroughly mixed and then heated to 90° C. for 3 minutes to denature the glycoproteins. The sample was cooled to room temperature for 2 minutes.

Digestion Step:

A 2 µl aliquot of a 1:1 mixture of 1 mg/ml PNGase F: 750 mM HEPES pH8 was added to each of the cooled samples and the samples were incubated at 50° C. for 5 minutes to release the N-glycans. The samples were cooled to room temperature for 2 minutes.

Labeling Step:

A 1:1 mixture of 0.2 M 2-diethylaminoethyl 4-[(2,5-dioxopyrrolidin-1-yl)oxycarbonylamino]benzoate ("InstantPC™"). in DMF: 1 M TMD in DMF was freshly prepared. Five µl of the mixture was added to the sample to label the released glycosylamines. The labeling was allowed to proceed for 2 minutes.

Cleanup Step:

The labeled glycans were resuspended in 200 µl of acetonitrile containing 1% formic acid and the solution was loaded onto GlykoPrep® Cleanup Cartridges (ProZyme, Inc., Hayward, Calif.). The cartridges were spun at 300×g for 3 minutes. The cartridges were washed with 200 µl of a 2.5% solution of formic acid in ACN for an additional 3 minutes at 300×g. The samples were eluted with 100 µl of a solution of 160 mM ammonium formate, pH 6.5 containing 10% ACN.

Analysis Steps

One µl of eluted sample was injected for high performance liquid chromatography (HPLC) analysis.

Example 3

This Example reports the results of the studies reported in Example 2.

Figure 1:
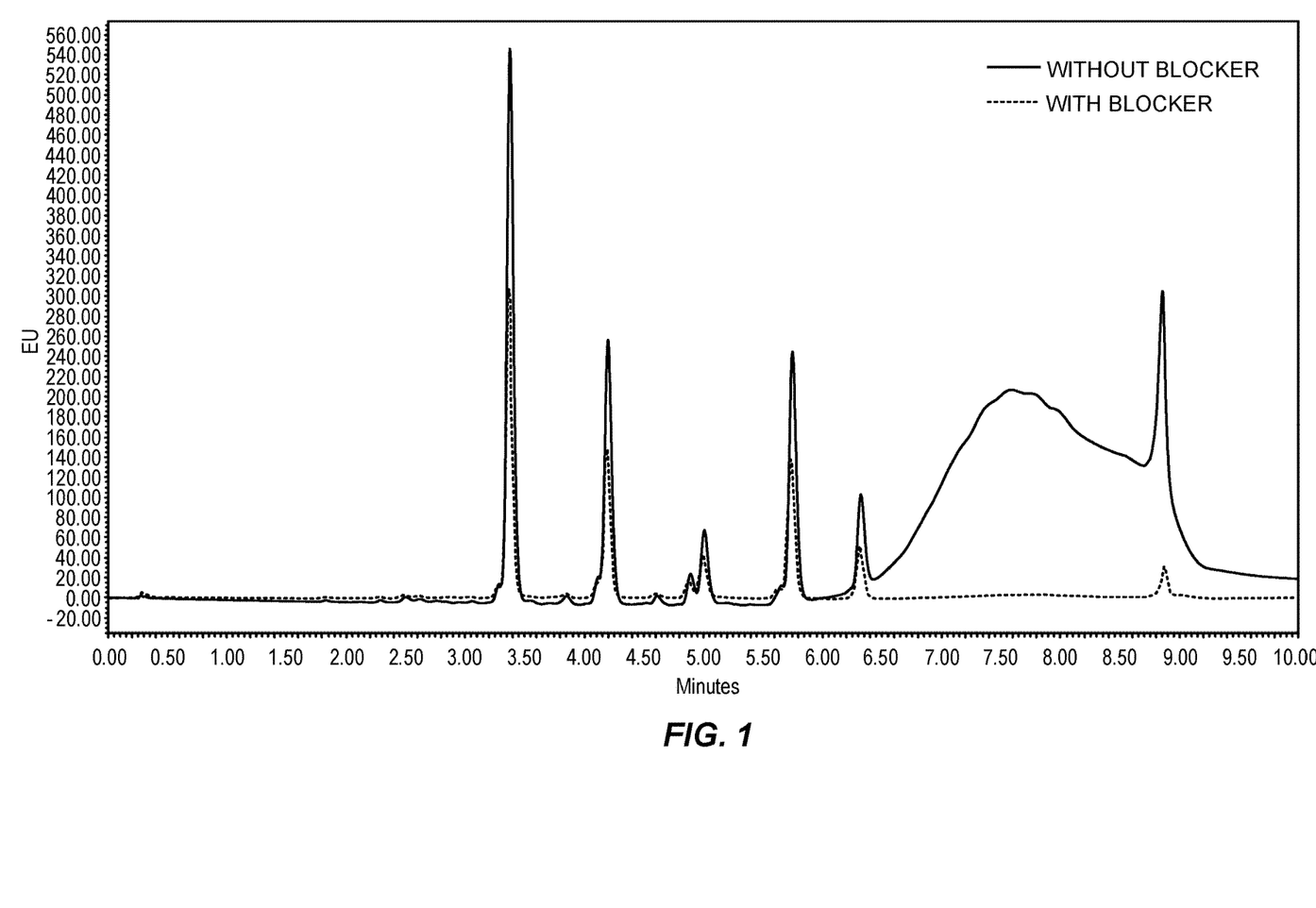
FIG. 1 is a graph of a HPLC analysis of molecules in a solution resulting from the denaturing and deglycosylation of an exemplar glycoprotein, RNase b, in the absence (solid line) or presence (dashed line) of an exemplar mild electrophile, DL-glyceraldehyde ("Blocker") in water. Molecules present in the solution, including glycans released from the glycoprotein and any other molecules present in the solution reactive with the label at the time of labeling were then labeled with the label InstantPC™. The resulting solution was then subjected to a clean-up step to remove unbound label and larger proteins prior to HPLC analysis. Y-axis: emission units ("EU"). X-axis: time, in minutes.

FIG. 1 is a graph showing the results of a high performance liquid chromatography ("HPLC") analysis of assays conducted using RNase b as the exemplar glycoprotein and InstantPC™ as the dye. Emissions units, or "EU," are shown on the Y axis, while time in minutes is shown on the X axis. As shown in the legend of the graph, the dashed line shows the results in the absence of (DL)-glyceraldehyde in water (the "blocker"), while the solid line shows the results when the blocker was present.

Figure 2:
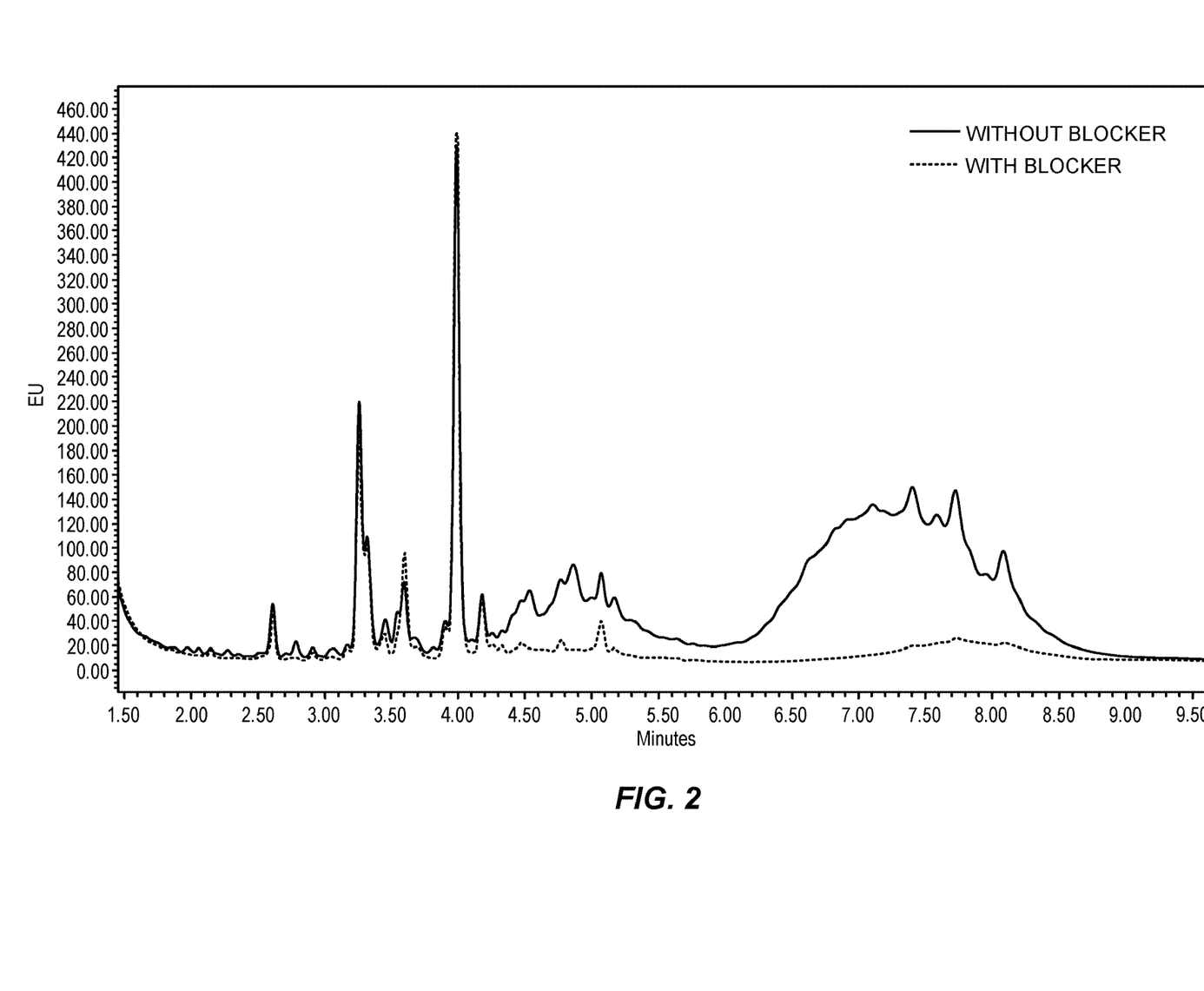
FIG. 2 is a graph of a HPLC analysis of a solution resulting from the denaturing and deglycosylation of an exemplar glycoprotein, Bovine Thyrotropic Hormone, in the absence (solid line) or presence (dashed line) of an exemplar mild electrophile, DL-glyceraldehyde ("Blocker") in water. Glycans released from the glycoprotein and any other molecules present in the solution reactive with the label at the time of labeling were then labeled with the label InstantPC™. Y-axis: emission units ("EU"). X-axis: time, in minutes.

FIG. 2 is a graph showing the results of a HPLC analysis of assays conducted using Bovine Thyrotropic Hormone as the exemplar glycoprotein and InstantPC™ as the dye. As for FIG. 1, emissions units, or "EU," are shown on the Y axis, while time in minutes is shown on the X axis. As shown in the legend of the graph, the dashed line shows the results in the absence of (DL)-glyceraldehyde in water (the "blocker"), while the solid line shows the results when the blocker was present.

FIGS. 1 and 2 both show a dramatic reduction in artifacts on the right side of the respective graphs in the assay run in the presence of the exemplar mild electrophile in comparison to the assay in the absence of the electrophile. As persons of skill will be aware, the glycans present on RNase b and on bovine thyrotropic hormone are known. With respect to FIG. 1, the "hump" and peak of the dotted line to the right of the 6.60 minute time point represent artifacts, not glycans. The hump is not seen in the solid line showing the presence of the blocker, and the peak at approximately 9 minutes is far smaller. With respect to FIG. 2, the peaks and long "hump" of the dotted line to the right of the 4.3 minute time point represent artifacts, not glycans. The peaks between approximately 4.3 minutes and 5.3 minutes seen in the absence of the blocker are much reduced or not present in the presence of the blocker, while the large hump between approximately 6.1 minutes and 8.6 minutes in the absence of the blocker is almost wholly absent in the presence of the blocker.

Example 4

This Example sets forth an exemplar workflow for denaturing and deglycosylating an exemplar glycoprotein in the presence of an exemplar mild electrophile, labeling amines released from the glycoprotein with a different dye, and analyzing the labeled glycans (and any labeled protein) using capillary electrophoresis.

Denaturation Step:

2 µl of 5% fatty acid detergent was added to 20 µl of a solution of 2 mg/ml desalted RNase b or TSH (40 µg of protein). For half of the samples, 2 µl of a solution of 100 mg/ml (DL)-glyceraldehyde ("the blocker") in water was added to the mixture; as a control, no blocker was added to the other half of the samples. The reagents were thoroughly mixed and then heated to 90° C. for 3 minutes to denature the glycoproteins. The samples were then cooled to room temperature for 2 minutes.

Digestion Step:

A 2 µl aliquot of a 1:1 mixture of 1 mg/ml PNGase F: 750 mM HEPES pH8 was added to each of the cooled samples and the samples were incubated at 50° C. for 5 minutes to release the N-glycans. The samples were cooled to room temperature for 2 minutes.

Labeling Step:

A 1:1:2 mixture of 0.05 M InstantQ™ in DMF: 1 M TMD in DMF:NMF was freshly prepared. Twenty µl of the mixture was added to the samples to label the released glycosylamines. The labeling was allowed to proceed for 2 minutes.

Cleanup Step:

A cleanup plate was prepared by rinsing the plate with 400 µl 5% Formic acid, 95% water. The cleanup plate was rinsed with 3×400 µl 95% Ethanol, 5% Formic acid. 400 µl of 100% ethanol was loaded to the cleanup plate, without vacuum. 150 µl of 100% ethanol was added to the samples, which were mixed several times and loaded onto the top of the 400 ul ethanol in the cleanup plate and immediately mixed. Vacuum was applied to load and the plate was washed 2× with 400 µl Ethanol, and eluted with 150 µl water prior to analysis using capillary electrophoresis.

Example 5

This Example reports the results of the studies reported in Example 4.

Figure 3:
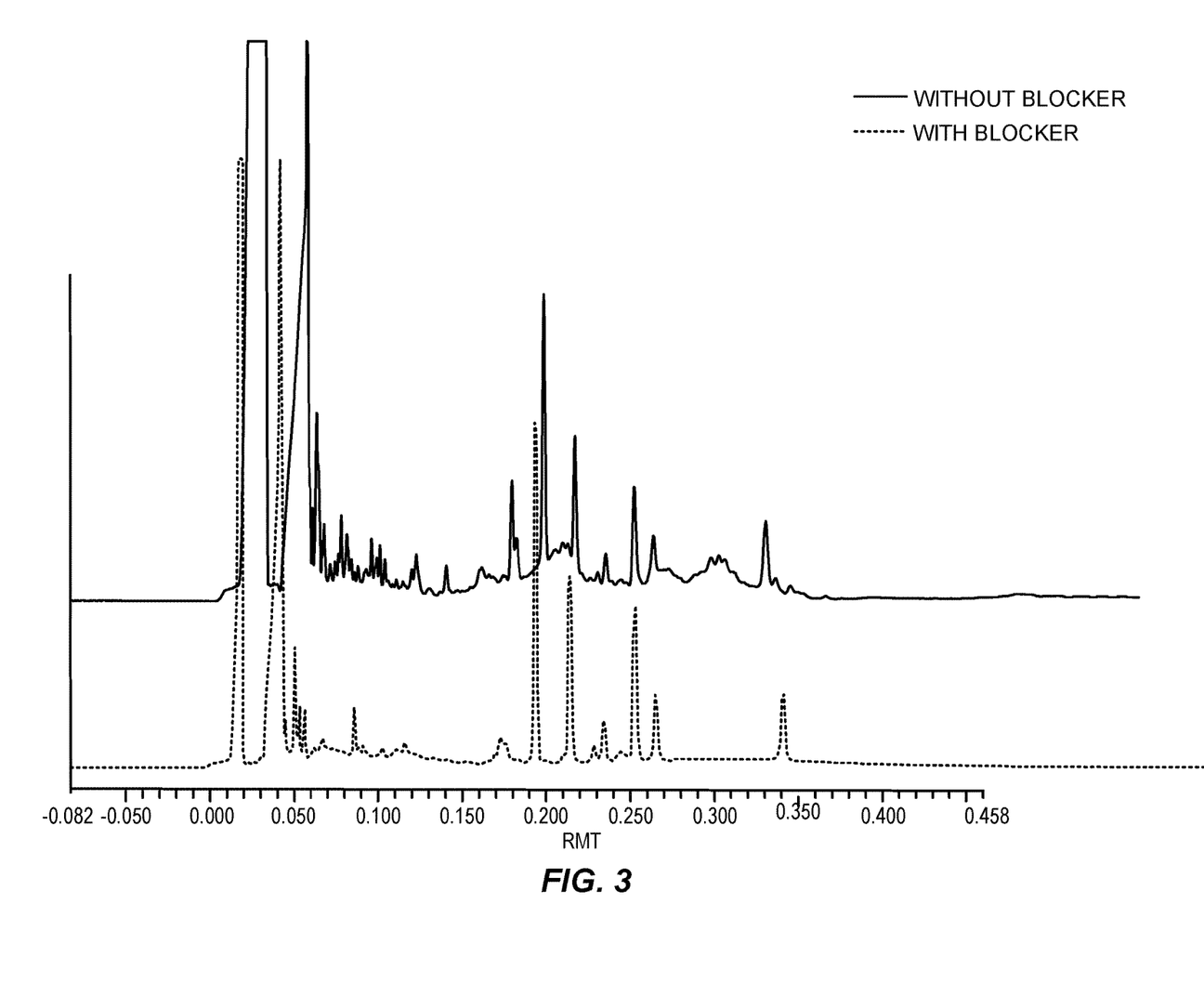
FIG. 3 is a graph of a capillary electrophoresis analysis with the Y-axis of the two lines on the graph offset from one another so that the two lines can be more clearly seen. An exemplar glycoprotein, RNase b, was denatured and deglycosylated in the absence (solid line) or presence (dashed line) of an exemplar mild electrophile, DL-glyceraldehyde ("Blocker") in water, and glycans released from the glycoprotein and any other molecules present in the solution reactive with the label at the time of labeling were then labeled with the label InstantQ™. Y-axis: relative fluorescence units ("RFU"). X-axis: Relative migration time "RMT".

FIG. 3 shows an analysis by capillary electrophoresis of the glycans released from RNase b in the presence (solid line) or absence (dashed line) of the blocker. The two lines have been offset on the Y-axis to facilitate the ability to see each line. Artifacts, presumably from labeling of the agycosylated protein, are much reduced.

Example 6

This Example reports the effect of studies of the effect of an exemplar mild electrophile on assays using a different labeling reagent and a different exemplar glycoprotein.

Denaturation and Deglycosylation Steps

RapiGest™ SF (Waters Corp., Milford, Mass.), 5% (w/v) was prepared by dissolving 10 mg of RapiGest™ SF Surfactant in 200 µl of Rapid Buffer in a tube and vortexing. 15.3 µl of water was dispensed into a 1 mL tube. 7.5 µl of 2 mg/mL EPO protein was added into the tube containing the RapiGest™ SF. Six µl of buffered, 5% (w/v) RapiGest™ SF solution was added to the tube, and aspirated to mix. For half of the samples, 2 µl of a solution of 100 mg/ml (DL)-glyceraldehyde ("the blocker") in water was added to the mixture, while the other half of the samples did not have blocker added. The samples were heated at least to 90° C. for 3 minutes and then cooled at room temperature for 3 minutes. 1.2 µl of Rapid PNGase F was added to the samples and aspirated to mix. The samples were incubated at 50° C. for 5 minutes and then cooled at room temperature for 3 minutes.

Labeling of Glycosylamines Step

335 µl of anhydrous DMF was added directly to one vial of 23 mg of RAPIFLUOR-MS® label (Waters Corp., Milford, Mass.) and mixed to solubilize. Twelve µl of the reagent solution was added to the deglycosylation mixture of the previous step and aspirated to mix and allow labeling. The labeling was allowed to proceed at room temperature for 5 minutes. The solution was then diluted with 358 µl of acetonitrile (ACN) and aspirated to mix.

Clean-Up Step

A GLYCOWORKS® HILIC µElution Plate (Waters Corp.) was set up, and shims or spacer and waste tray added. Wells were conditioned by adding 200 µl of water per well. Wells were equilibrated by adding 200 µl 85% ACN. ACN-diluted samples were loaded (~400 µl per well). Wells were washed with two 600 µl volumes of 1% formic acid, 90% ACN. The waste tray was replaced with a sample collection tray loaded with 600 µl tubes. Glycans were eluted with three 30 µl volumes of Water' solid phase elution ("SPE") buffer into 600 µl tubes. SPE eluate was diluted with 100 µl of DMF and 210 µl of ACN and aspirated to mix prior to HPLC analysis.

Example 7

This Example discusses the results of the studies reported in Example 6.

Figure 4:
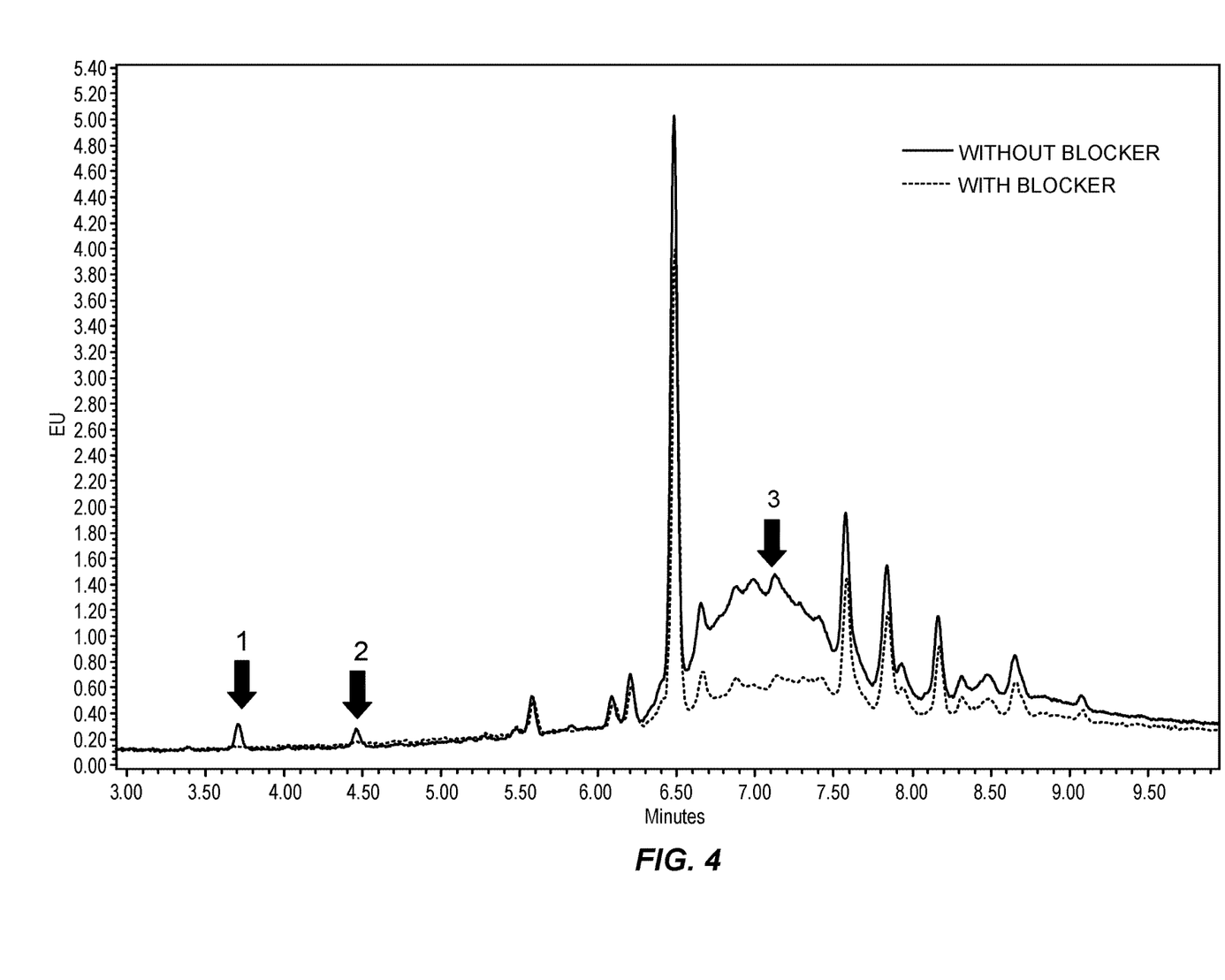
FIG. 4 is a graph of a HPLC analysis of the solution resulting from the denaturing and deglycosylation of an exemplar glycoprotein, epoetin alfa, in the absence (solid line) or presence (dashed line) of an exemplar mild electrophile ("blocker"). Glycans released from the glycoprotein and any other molecules present in the solution reactive with the label at the time of labeling were then labeled with the label RAPIFLUOR-MS®. Y-axis: emission units ("EU"). X-axis: time, in minutes. The arrows denote areas in which artifacts in the HPLC solution have been diminished by the presence of the mild electrophile during the denaturation and labeling steps compared to the solution in a mild electrophile was not present.

FIG. 4 shows the HPLC analysis of the samples discussed in Example 6. The vertical arrows show three points at which the presence of the blocker eliminates or sharply reduced artifacts compared to the same assay in the absence of the blocker.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. An in vitro method of labeling glycosylamines released from a glycoprotein or glycopeptide of interest, said method comprising:
   (a) forming a mixture of said glycoprotein or glycopeptide and a mild electrophile in a solution,
   (b) incubating said mixture in said solution at a first temperature and for a time sufficient to denature said glycoprotein or glycopeptide,
   (c) reducing said temperature of said mixture in said solution to a second temperature, which second temperature is suitable for enzymatic deglycosylation of said glycoprotein or glycopeptide,
   (d) contacting said glycoprotein or glycopeptide at said second temperature with at least one deglycosylation enzyme which releases glycans from a glycoprotein or glycopeptide as glycosylamines, thereby releasing glycans from said glycoprotein or glycopeptide as glycosylamines, and
   (e) contacting said released glycosylamines with an amine-reactive dye under conditions allowing said amine-reactive dye to label said released glycosylamines, thereby labeling said released glycosylamines; wherein said mild electrophile is DL-glyceraldehyde, glyceraldehyde dimer, glycoaldehyde dimer, erythrose, pyruvaldehyde, 2-ethylbutyraldehyde, 2-m ethylbutyraldehyde, 2-m ethylvaleraldehyde, 4-methyl-4-nitrovaleraldehyde, acetaldehyde, butyraldehyde, isobutyraldehyde, propionaldehyde, or valeraldehyde.

2. The method of claim 1, wherein said first temperature is 90° C. or higher.

3. The method of claim 1, wherein said solution further comprises a detergent.

4. The method of claim 1, wherein said at least one deglycosylation enzyme which releases glycans from said glycoprotein or glycopeptide as glycosylamines is PNGase F.

5. The method of claim 1, wherein said mild electrophile is DL-glyceraldehyde, glyceraldehyde dimer, or glycoaldehyde dimer.

6. The method of claim 1, wherein said mild electrophile is DL-glyceraldehyde.

7. The method of claim 1, wherein said mild electrophile is glyceraldehyde dimer.

8. The method of claim 1, wherein said mild electrophile is glycoaldehyde dimer.

9. The method of claim 1, wherein said glycoprotein of interest is an antibody.

10. The method of claim 1, wherein said contacting of released glycosylamines with said amine-reactive dye in step (e) is within 30 minutes of release from said glycoprotein or glycopeptide.

11. The method of claim 1, wherein said contacting of released glycosylamines with said amine-reactive dye in step (e) is within 15 minutes of release from said glycoprotein or glycopeptide.

12. The method of claim 1, wherein said contacting of released glycosylamines with said amine-reactive dye in step (e) is within 1 minute of release of said glycosylamines from said glycoprotein or glycopeptide.

13. The method of claim 1, wherein said amine-reactive dye is selected from the group consisting of (2-(diethylamino)ethyl 4-[(2,5-dioxopyrrolidin-1-yl)oxycarbonylamino]benzoate) (InstantPC™), 8-[(2,5-dioxopyrrolidin-1-yl)oxycarbonylamino]naphthalene-1,3,5-trisulfonic acid ("Amine-reactive ANTS™"), 4-[(2,5-dioxopyrrolidin-1-yl)oxycarbonylamino]benzoic acid ("InstantAA™"), (7-[(2,5-dioxopyrrolidin-1-yl)oxycarbonylamino]naphthalene-1,3,6-trisulfonic acid) ("InstantQ™"), and RAPIFLUOR-MS®.

14. The method of claim 1, wherein said released glycosylamines are at or at about room temperature when contacted with said amine-reactive dye.

15. The method of claim 1, further comprising either:
   step (f), providing said labeled glycosylamines to an analytical means, or
   step (f') subjecting said labeled glycosylamines to a solid phase extraction means that reduces the amount of mild electrophile present, to obtain labeled glycosylamines with a reduced amount of said mild electrophile present, and step (f") providing said labeled glycosylamines with said reduced amount of said mild electrophile present to an analytical means.

16. The method of claim 15, wherein said solid phase extraction means is a solid phase cartridge.

17. The method of claim 15, wherein said analytical means is selected from the group consisting of high-pressure liquid chromatography, capillary electrophoresis, fluorescence analysis, mass spectrometry, and a combination of any of these.

18. The method of claim 1, wherein said glycoprotein of interest is in a biological sample.

19. The method of claim 18, wherein said biological sample is selected from the group consisting of: a cell culture supernatant, a membrane protein preparation, milk, a tissue sample, cerebrospinal fluid, plasma, serum, urine, a respiratory secretion, bile synovial fluid, pleural fluid, lymph, tears, saliva, and a stool sample.

20. The method of claim 19, wherein said biological sample is milk.

21. A composition, comprising: (i) a detergent, (ii) a mild electrophile, (iii) at least one deglycosylation enzyme which releases glycans from a glycoprotein as glycosylamines, (iv) a partially or fully deglycosylated protein or peptide from which glycans have been removed by said deglycosylation enzyme, and (v) glycosylamines released from said partially or fully deglycosylated protein by said enzyme; wherein said mild electrophile is DL-glyceraldehyde, glyceraldehyde dimer, glycoaldehyde dimer, erythrose, pyruvaldehyde, 2-ethylbutyraldehyde, 2-m ethylbutyraldehyde, 2-m ethylvaleraldehyde, 4-methyl-4-nitrovaleraldehyde, acetaldehyde, butyraldehyde, isobutyraldehyde, propionaldehyde, or valeraldehyde.

22. The composition of claim 21, further wherein said glycoprotein is an antibody.

23. The composition of claim 21, further wherein said deglycosylation enzyme is PNG F.

24. The method of claim 21, wherein said mild electrophile is DL-glyceraldehyde, glyceraldehyde dimer, or glycoaldehyde dimer.

25. The method of claim 21, wherein said mild electrophile is DL-glyceraldehyde.

26. An in vitro method of reducing artifacts in analyzing glycans released from a glycoprotein or glycopeptide and labeled by reductive amination, said method comprising the following steps in the following order:
   (a) forming a solution comprising said glycoprotein or glycopeptide, and a mild electrophile, under conditions allowing said mild electrophile to block any nucleophilic components present in said solution or on said glycoprotein or glycopeptide,
   (b) heating said solution to a first temperature, and for a time, sufficient to denature said glycoprotein or glycopeptide, (c) reducing said temperature of said solution to a second, cooler temperature,
(d) releasing glycans from said glycoprotein or glycopeptide,
(e) labeling said glycans released from said glycoprotein or glycopeptide by reductive amination, and
(f) analyzing said glycans labeled by said reductive amination, whereby said blocking of said nucleophilic components present in said solution or on said glycoprotein or glycopeptide prior to said denaturation and reductive amination reduces artifacts in said analysis of said released glycans; wherein said mild electrophile is DL-glyceraldehyde, glyceraldehyde dimer, glycoaldehyde dimer, erythrose, pyruvaldehyde, 2-ethylbutyraldehyde, 2-m ethylbutyraldehyde, 2-m ethylvaleraldehyde, 4-methyl-4-nitrovaleraldehyde, acetaldehyde, butyraldehyde, isobutyraldehyde, propionaldehyde, or valeraldehyde.

27. The method of claim 26, wherein said mild electrophile is DL-glyceraldehyde, glyceraldehyde dimer, or glycoaldehyde dimer.

28. The method of claim 26, wherein said mild electrophile is DL-glyceraldehyde.

29. The method of claim 26, wherein said mild electrophile is glyceraldehyde dimer.

30. The method of claim 26, wherein said mild electrophile is glycoaldehyde dimer.

31. The method of claim 26, wherein said glycoprotein is an antibody.

32. The method of claim 26, wherein said glycoprotein of interest is in a biological sample.

33. The method of claim 32, wherein said biological sample is selected from the group consisting of: a cell culture supernatant, a membrane protein preparation, milk, a tissue sample, cerebrospinal fluid, plasma, serum, urine, a respiratory secretion, bile synovial fluid, pleural fluid, lymph, tears, saliva, and a stool sample.

34. The method of claim 33, wherein said biological sample is milk.

35. The method of claim 26, wherein said solution further comprises a detergent.

36. The method of claim 26, wherein said analysis is selected from the group consisting of high-pressure liquid chromatography, capillary electrophoresis, fluorescence analysis, mass spectrometry, and a combination of any of these.

37. A method of reducing artifacts in analyzing glycans released from a glycoprotein or glycopeptide without labeling, said method comprising the following steps in the following order:
(a) forming a solution comprising said glycoprotein or glycopeptide, and a mild electrophile, under conditions allowing said mild electrophile to block any nucleophilic components present in said solution or on said glycoprotein or glycopeptide,
(b) heating said solution to a first temperature, and for a time, sufficient to denature said glycoprotein or glycopeptide,
(c) reducing said temperature of said solution to a second, cooler temperature,
(d) releasing glycans from said glycoprotein or glycopeptide, and
(e) analyzing said glycans labeled by said reductive amination, whereby said blocking of said nucleophilic components present in said solution or on said glycoprotein or glycopeptide prior to said denaturation reduces artifacts in said analysis of said released glycans; wherein said mild electrophile is DL-glyceraldehyde, glyceraldehyde dimer, glycoaldehyde dimer, erythrose, pyruvaldehyde, 2-ethylbutyraldehyde, 2-methylbutyraldehyde, 2-m ethylvaleraldehyde, 4-methyl-4-nitrovaleraldehyde, acetaldehyde, butyraldehyde, isobutyraldehyde, propionaldehyde, or valeraldehyde.

38. The method of claim 37, wherein said analysis is by mass spectrometry, High-performance Anion Exchange Chromatography coupled with Pulsed Amperometric Detection ("HPAE-PAD"), Charged Aerosol Detection ("CAD"), Evaporative Light Scattering Detection ("ELSD"), or a combination of any of these.

* * * * *